Figure 1:
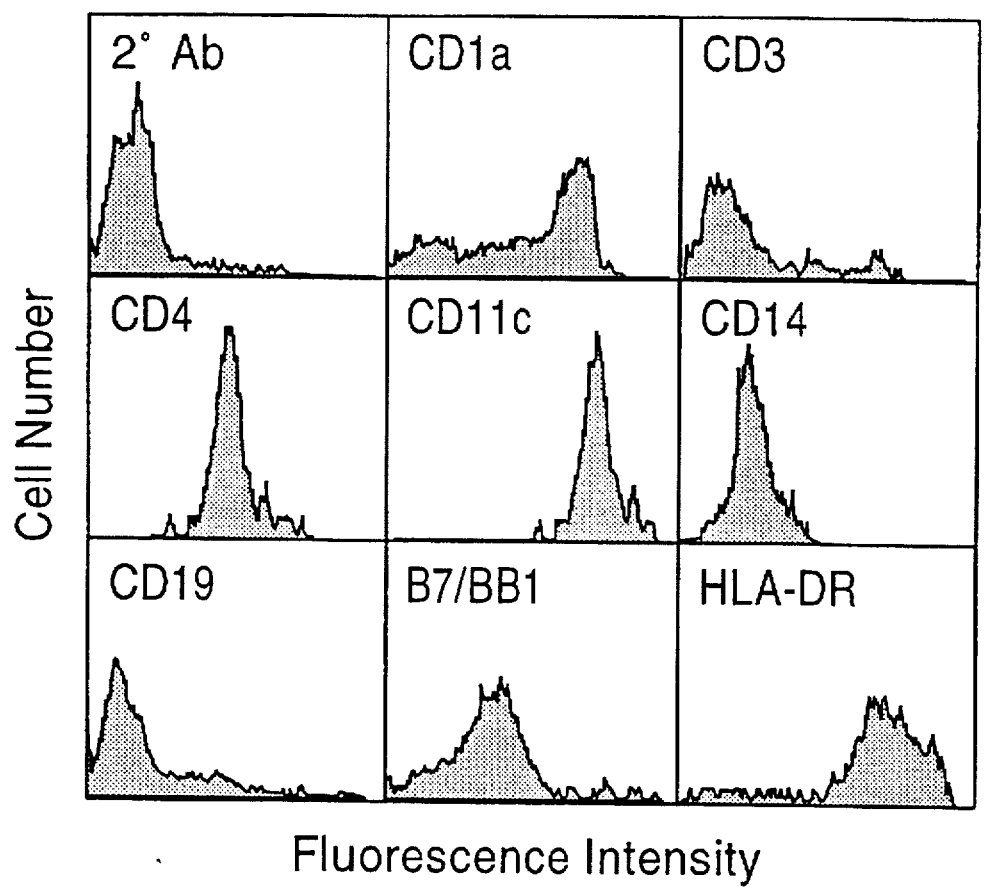

United States Patent [19]
Murphy et al.

[11] Patent Number: 5,788,963
[45] Date of Patent: Aug. 4, 1998

[54] ISOLATION AND/OR PRESERVATION OF DENDRITIC CELLS FOR PROSTATE CANCER IMMUNOTHERAPY

[75] Inventors: Gerald P. Murphy, Seattle; Alton L. Boynton, Redmond; Benjamin A. Tjoa, Seattle, all of Wash.

[73] Assignee: Pacific Northwest Cancer Foundation, Seattle, Wash.

[21] Appl. No.: 509,254

[22] Filed: Jul. 31, 1995

[51] Int. Cl.$^6$ ................................................ A01N 63/00
[52] U.S. Cl. ............................ 424/93.21; 424/185.1; 424/277.1
[58] Field of Search .................... 424/93.21, 185.1, 424/277.1; 530/810; 435/240.1

[56] References Cited

U.S. PATENT DOCUMENTS

| | | | |
|---|---|---|---|
| 5,004,681 | 4/1991 | Boyse et al. | 435/2 |
| 5,162,504 | 11/1992 | Horoszewicz | 530/388.2 |
| 5,192,553 | 3/1993 | Boyse et al. | 424/529 |
| 5,227,471 | 7/1993 | Wright, Jr. | 530/388.2 |
| 5,314,996 | 5/1994 | Wright, Jr. | 530/387.3 |

FOREIGN PATENT DOCUMENTS

| | | |
|---|---|---|
| WO 91/13632 | 9/1991 | WIPO. |
| WO 94/02156 | 2/1994 | WIPO. |
| WO 94/21287 | 9/1994 | WIPO. |
| WO95/34638 | 12/1995 | WIPO. |

OTHER PUBLICATIONS

Israeli et al., (1993) "Molecular Cloning of a Complementary DNA Encoding a Prostate-specific Membrane Antigen", Cancer Research 53: 227–230.

Abdul, M., et al. (1995) "Secretion of Prostate-Specific Antigen-Suppressing Activity by Two Human Prostate Carcinoma Cell Lines", Urol. Oncol., vol. 1, pp. 38–41.

Alijagic, S., et al. (1995) "Dendritic Cells Generated From Peripheral Blood Transfected with Human Tyrosinase Induced Specific T Cell Activation", European Journal of Immunology, vol. 25, pp. 3100–3107.

Becker, Y. (1992) "Anticancer Role of Dendritic Cells (DC) in Human and Experimental Cancers–A Review", Anticancer Research, vol. 12, pp. 511–520.

Becker, Y. (1993) "Success and Failure of Dendritic Cell (DC) Anticancer Activity May Be Modulated by Nitric Oxide Synthetase (NOS) Gene Expression: A Hypothesis", in vivo, vol. 7, pp. 285–288.

Beckett, M.L., et al. (1991) "Monoclonal Antibody PD41 Recognizes an Antigen Restricted to Prostate Adenocarcinomas", Cancer Research, vol. 51, pp. 1326–1333.

Beckett, M.L. and Wright, G.L. (1995) "Characterization of a Prostate Carcinoma Mucin-Like Antigen (PMA)", Int. J. Cancer, vol. 62, pp. 703–710.

Bernhard, H., et al. (Mar. 1995) "Generation of Immunostimulatory Dendritic Cells from Human CD34+ Hematopoietic Progenitor Cells of the Bone Marrow and Peripheral Blood", Cancer Research vol. 55, pp. 1099–1104.

Beverley, P.C.L. and Abbas, A.K. (Sep. 23, 1994) "The Scientific Challenge of Langerhans Cell Histiocytosis", British Journal of Cancer–Suppl., pp. S61–S63.

Chaux, P., et al. (1993) "Surface Phenotype and Functions of Tumor–infiltrating Dendritic Cells: CD8 Expression by a Cell Subpopulation", European Journal of Immunology, vol. 23, pp. 2517–2525.

Cohen, P.A., et al. (Feb. 15, 1994) "CD4+ T-Cells from Mice Immunized to Syngeneic Sarcomas Recognize Distinct, Non–Shared Tumor Antigens", Cancer Research, vol. 54, pp. 1055–1058.

Cohen, P. J., et al. (1994) "Murine epidermal Langerhans Cells and Splenic Dendritic Cells Present Tumor–associated Antigens to Primed T Cells", European Journal of Immunology, vol. 24, pp. 315–319.

Croft, M., et al. (Nov. 1994) "Generation of Polarized Antigen–specific CD8 Effector Populations: Reciprocal Action of Interleukin (IL)–4 and IL–12 in Promoting Type 2 versus Type 1 Cytokine Profile", Journal of Experimental Medicine, vol. 180, pp. 1715–1728.

Wright, G.L., et al. (1990) "Characterization of a New Prostate Carcinoma–associated Marker: 7E11–C5", in Antibody, Immunoconjugates and Radiopharmaceuticals, vol. 3, No. 1, pp. 89 (Abstract #193).

Feng, et al. (1991) "Purification and Biochemical Characterization of the 7E11–C5 Prostate Carcinoma–Associated Antigen", Proc. Am. Assoc. Cancer Res. vol. 32 (Abs #1418), p. 238.

Freudenthal, P.S and Steinman, R.M. (1990) "The Distinct Surface of Human Blood Dendritic Cells, as Observed After an Improved Isolation Method", Proc. Natl. Acad. Sci. U.S.A. vol. 87, pp. 7698–7702.

Haskell, et al. (1978) "Systemic and Local Immunity in Allograft and Cancer Rejection", Contemp. Top. Immunol., vol. 8, pp. 107–170.

Hauser, C., et al. (1989) "Characterization of Primary T Helper Cell Activation and T Cell Lines Stimulated by Hapten–modified, Cultured Langerhans Cells", Journal of Investigative Dermatology, vol. 93, No. 5, pp. 649–655.

(List continued on next page.)

*Primary Examiner*—Toni R. Scheiner
*Attorney, Agent, or Firm*—Pennie & Edmonds LLP

[57] ABSTRACT

Methods and compositions for use of human dendritic cells to activate T cells for immunotherapeutic responses against primary and metastatic prostate cancer are disclosed. In one embodiment, human dendritic cells, after exposure to a prostate cancer antigen or specific antigenic peptide, are administered to a prostate cancer patient to activate the relevant T cell responses in vivo. In an alternate embodiment, human dendritic cells are exposed to a prostate cancer antigen or specific antigenic peptide in vitro and incubated or cultured with primed or unprimed T cells to activate the relevant T cell responses in vitro. The activated T cells are then administered to a prostate cancer patient. Methods and compositions for human dendritic cells with extended life span and cryopreserved dendritic cells are disclosed.

8 Claims, 9 Drawing Sheets

OTHER PUBLICATIONS

Hock, B.D., et al. (Dec. 1994) "Characterization of CMRF–44, A Novel Monoclonal Antibody to an Activation Antigen Expressed by the Allostimulatory Cells Within Peripheral Blood, Including Dendritic Cells", Immunology, vol. 83, No. 4, pp. 573–581.

Horoszewicz, J.S., et al. (1980) "The LNCaP Cell Line–A New Model for Studies on Human Prostatic Carcinoma", in *Models for Prostate Cancer*, Prog. Clin. Bio. Res., vol. 37, pp. 115–132.

Horoswewicz, J.S., et al. (1983) "LNCaP Model of Human Prostate Carcinoma", Cancer Research, vol. 43, pp. 1809–1818.

Horoszewicz, J.S., et al. (1987) "Monoclonal Antibodies to a New Antigenic Marker in Epithelial Prostate Cells and Serum of Prostatic Cancer Patients", Anticancer Research, vol. 7, pp. 927–936.

Hsu, F.J., et al. (Jan. 1996) "Vaccination of Patients with B–Cell Lymphoma Using Autologous Antigen–Pulsed Dendritic Cells", Nature Medicine, vol. 2, No. 1, pp. 52–58.

Israeli, et al. (1994 "Expression of the Prostate–specific Membrane Antigen", Cancer Research, vol. 54, p. 1807–1811.

Jones, T., et al. (1994) "Potential Role of Granulocyte–Macrophage Colony–Stimulating Factor as Vaccine Adjuvant", Eur. J. Clin. Microbio. Infect. Dis., vol. 13, Suppl. 2, pp. 47–53.

Kaminski, M.J., et al. (Sep. 1993) "Killing of Skin–derived Tumor Cells by Mouse Dendritic Epidermal T–Cells", Cancer Research, vol. 53, pp. 4014–4019.

Kessler, LI. (1993) "Epidemiological Considerations in the Role of Dendritic/Langerhans Cells in Human Cancer", in vivo, vol. 7, pp. 305–312.

Koch, F., et al. (1995) "Antigen Processing in Populations of Mature Murine Dendritic Cells is Caused by Subsets of Incompletely Matured Cells", Journal of Immunology, vol. 155, pp. 93–100.

Love–Schimenti, C.D. and Kripke, M.L. (Oct. 15, 1994) "Dendritic Epidermal T Cells Inhibit T Cell Proliferation and May Induce Tolerance by Cytotoxicity", Journal of Immunology, vol. 153, No. 8, pp. 3450–3456.

Love–Schimenti, C.D. and Kripke, M.L. (Mar. 1994) "Inhibitory Effect of a Dendritic Epidermal T Cell Line on K1735 Melanoma Cells in vivo and in vitro", Journal of Leukocyte Biology, vol. 55, pp. 379–384.

Macatonia, S.E., et al. (1989) "Suppression of Immune Responses by Dendritic Cells Infected with HIV", Immunology, vol. 67, pp. 285–289.

Macatonia, S.E., et al. (Apr. 1989) "Primary Stimulation by Dendritic Cells Induces Antiviral Proliferative and Cytotoxic T Cell Responses in vitro", Journal of Experimental Medicine, vol. 169, pp. 1255–1264.

Macatonia, S.E., et al. (1991) "Primary Proliferative and Cytotoxic T–Cell Responses to HIV Induced in vitro by Human Dendritic Cells", Immunology, vol. 74, pp. 399–406.

Markowicz, S. and Engleman, E.G. (Mar. 1990) "Granulocyte–Macrophage Colony–stimulating Factor Promotes Differentiation and Survival of Human Peripheral Blood Dendritic Cells in Vitro", J. Clin. Invest., vol. 85, pp. 955–961.

Markowicz, S. and Mehta, A. (1993) "The Effect of Human Dendritic Cells on the Lectin–induced Responsiveness of CD4+ T Cells to IL–2 and IL–4", in *Dendritic Cells in Fundamental and Clinical Immunology*, ed. Kamperdijk, et al., pp. 75–80.

McCormack, R.T., et al. (May 1995) "Molecular Forms of Prostate–Specific Antigen and the Human Kallikrein Gene Family: A New Era", Urology, vol. 45, No. 5, pp. 729–744.

Melief, C.J.M. and Kast, W.M. (1992) "Lessons from T Cell Responses to Virus Induced Tumours for Cancer Eradication in General", in *Cancer Surveys vol. 13: A New Look At Tumour Immunology*, pp. 81–99.

Mukherji, B., et al. (Aug. 1995) "Induction of Antigen–Specific Cytolytic T Cells in situ in Human Melanoma by Immunization with Synthetic Peptide–Pulsed Autologous Antigen Presenting Cells", Proceeding of the National Academy of Sciences, vol. 92, pp. 8078–8082.

Murphy, G.P. (1995) "Radioscintiscanning of Prostate Cancer", Cancer Supplement, vol. 75, No. 7, pp. 1819–1822.

Neff, D.N. (Jan. 1996) "Anti–Lymphoma Vaccine Scores, Deploying Dendritic Cells, Private Tumor Antigens", BioWorld Today, vol. 7, No. 8, pp. 1 and 3.

O'Doherty, U., et al. (Sep. 1993) "Dendritic Cells Freshly Isolated from Human Blood Express CD4 and Mature into Typical Immunostimulatory Dendritic Cells after Culture in Monocyte–Conditioned Medium", J. Exp. Med., vol. 178, pp. 1067–1078.

Okada, C.Y. and Rechsteiner, M. (1982) "Introduction of Macromolecules into Culture Mammalian Cells by Osmotic Lysis of Pinocytic Vesicles", Cell, vol. 29, pp. 33–41.

Papsidero, L.D., et al. (Jul. 1980) "A Prostate Antigen in Sera of Prostatic Cancer Patients", Cancer Research, vol. 40, pp. 2428–2432.

Pardoll, D. (1992) "New Strategies for Active Immunotherapy with Genetically Engineered Tumor Cells", Curr. Opin. Immunol., vol. 4, pp. 619–923.

Poste, et al. (1976) "Lipid Vesicles as Carriers for Introducing Biological Active Materials into Cells", in Methods Cell Biol., vol. 14, pp. 33–71.

Puccetti, P., et al. (1994) "Use of a Skin Test Assay to Determine Tumor–specific CD8+ T Cell Reactivity", Eur. J. Immunol., vol. 24, pp. 1446–1452.

Reddy, R. et al. (1991) "pH Sensitive Liposomes Provide an Efficient Means of Sensitizing Target Cells to Class I Restricted CTL Recognition of a Soluble Protein", J. Immunol. Methods, vol. 141, pp. 157–163.

Romani, N. et al. (Jul. 1994) "Proliferating Dendritic Cell Progenitors in Human Blood", J. Exp. Med. vol. 180, pp. 83–93.

Sallusto F. and Lanzavecchia, A. (Apr. 1994) "Efficient Presentation of Soluble Antigen by Cultured Human Dendritic Cells Is Maintained by Granulocyte/Macrophage Colony–stimulating Factor Plus Interleukin 4 and Down-regulated by Tumor Necrosis Factor $\alpha$", J. Exp. Med., vol. 179, pp. 1109–1118.

Srivastava, B.I., et al. (1994) "Phenotype, Genotype and Cytokine Production in Acute Leukemia Involving Progenitors of Dendritic Langerhans' Cells", Leukemia Research, vol. 18, No. 7, pp. 499–511.

Steinman, R.M. (1991) "The Dendritic Cell System and Its Role in Immunogenicity", Ann. Rev. Immunol., vol. 9, pp. 271–296.

Szakal, A.K. and Tew, J.G. (Oct. 1992) "Follicular Dendritic Cells: B–Cell Proliferation and Maturation", Cancer Research (Suppl.), vol. 52, pp. 5554s–5556s.

Troyer, J.K., et al. (1995) "Biochemical Characterization and Mapping of the 7E11–C5.3 Epitope of the Prostate–Specific Membrane Antigen", Urol. Oncol., vol. 1, pp. 29–37.

Tsujitani, S., et al. (1992) "Postoperative Adjuvant Immunochemotherapy and Infiltration of Dendritic Cells for Patients with Advanced Gastric Cancer", Anticancer Research, vol. 12, pp. 645–648.

Tsujitani, S., et al. (1993) "Dendritic Cells Prevent Lymph Node Metastasis in Patients with Gastric Cancer", in vivo, vol. 7, pp. 233–238.

Tsujitani, S., et al. (Mar. 1995) "Infiltration of Dendritic Cells into Regional Lymph Nodes in Gastric Cancer", Cancer, vol. 75, No. 6 Suppl., pp. 1478–1483.

Vose, B.M. and Moore, M. (Jan. 1985) "Human Tumor–Infiltrating Lymphocytes: A Marker of Host Response", Seminars in Hematology, vol. 22, No. 1, pp. 27–40.

Welsh, E.A. and Kripke, M.L. (Feb. 1990) "Murine Thy–1 +Dendritic Epidermal Cells Induce Immunologic Tolerance in Vivo", Journal of Immunology, vol. 144, No. 3, pp. 883–891.

Wright, Jr., G.L. et al. (Nov. 1983) "Immunohistochemical Localization of Prostate Carcinoma–associated Antigens", Cancer Research, vol. 43, pp. 5509–5516.

Wright, Jr., G.L., et al. (1995) "Expression of Prostate–Specific Membrane Antigen in Normal, Benign, and Malignant Prostate Tissues", Urol. Oncol., vol. 1, pp. 18–28.

Young, J.W. and Steinman, R.M. (Apr. 1990) "Dendritic Cells Stimulate Primary Human Cytolytic Lymphocyte Responses in the Absence of CD4+ Helper T Cells", J. Exp. Med., Vol. 171, pp. 1315–1332.

Zöller, M. (1991) "Intrathymic Presentation by Dendritic Cells and Macrophages: Their Role in Selecting T Cells With Specificity for Internal and External Nominal Antigen", Immunology, vol. 74, pp. 407–413.

Becker et al., (1991) "Biochemical Properties of MHC Class II Molecules Endogenously Synthesized and Expressed by Mouse Langerhans Cells", Eur. J. Immunol. 21:1213–1220.

Blauvelt et al., (1995) "Functional Studies of Epidermal Langerhans Cells and Blood Monocytes in HIV–Infected Persons", J. Immunol. 154:3506–3515.

Caux et al., (1992) "GM–CSF and TNF–$\alpha$ Cooperate in the Generation of Dendritic Langerhans Cells", Nature, 360:258–261.

Dezutter–Dambuyant, (1995) "Données Récentes et Recherces en Cours Sur la Cellulle de Langerhans Épidermique", Path. Biol., 43(10):841–847 (English Abstract).

Dubois et al., (1995) "Différentiation In Vitro et Fonctions des Cellules Dendritiques Obtenues a Partir de Précurseurs Hématopoiétiques CD34$^+$", Path. Biol. 43(10):829–840 (English Abstract).

Heinen (1995) "Les Cellules Dendritiques Folliculaires: Phénotype, Origine et Fonctions", Path. Biol. 43(10):848–857 (English Abstract).

Mommaas et al., (1995) "Distribution of HLA Class II Molecules in Epidermal Langerhans Cells In Situ", Eur. J. Immunol. 25:520–525.

Kampgen et al., (1991) "Class II Major Histocompatibility Complex Molecules of Murine Dendritic Cells: Synthesis, Sialylation of Invariant Chain, and Antigen Processing Capacity are Down–Regulated Upon Culture", Proc. Natl. Acad. Sci., 88:3014–3018.

Staquet, (1995), "Adhérence et Migration des Cellules Dendritiques Épidermiques", Pat. Biol., 43(10):858–862 (English Abstract).

Thomas et al., (1993) "Isolation and Characterization of Human Peripheral Blood Dendritic Cells", J. Immunol., 150(3):821–834.

Lutz MB et al (1994) J. Immunol. Methods 174: 269–279.

Taylor M.J. (1990) Cryobiology 27:269–278.

ISOLATION AND/OR PRESERVATION OF DENDRITIC CELLS FOR PROSTATE CANCER IMMUNOTHERAPY

FIELD OF THE INVENTION

The present invention relates to compositions and methods of isolating and/or preserving and using human dendritic cells for immunotherapy for cancer. In particular, the invention relates to methods for the use of dendritic cells for the activation and expansion of large numbers of prostate antigen specific T cells for use in adoptive cellular immunotherapy against prostate cancer, as well as methods for the use of prostate antigen pulsed dendritic cells as vaccines and/or immunotherapeutics to slow or inhibit the growth of primary or metastatic prostate cancer.

BACKGROUND OF THE INVENTION

2.1. PROSTATE CANCER

Prostate cancer is the second leading cause of death from cancer among men. In fact, prostate cancer is the most common (noncutaneous) cancer diagnosed in the American male and is steadily increasing, as a result of the increasing population of older men as well as greater awareness and earlier diagnosis of the disease. See, Wright et al., 1995, Urol. Oncol. 1: 18–28. In 1995, it is projected that over 244,000 men will be diagnosed with prostate cancer in this year. There will be 40,400 deaths. The life time risk for men, to suffer prostate cancer is now 1 in 8 for Caucasians, and an estimated 1 in 7 for African Americans. High risk groups are those with a positive family history or African Americans. Over a lifetime, above 25% of the men diagnosed with prostate cancer will die of the disease. Wingo et al., 1995, CA Cancer J. Clin. 45(2):8–30. Moreover, many patients who do not die of prostate cancer require treatment to ameliorate symptoms such as pain, bleeding, and urinary obstruction. Thus, prostate cancer is also a major cause of suffering and of health care expenditures. Catalona, W. J., 1994, New Eng. J. Med. 331: 996–1004.

Cytotoxic chemotherapy is largely ineffective in treating prostate cancer. A combination of agents is no more effective than a single agent, and the addition of chemotherapy to hormonal therapy does not improve survival. Eisenberger, M. A., 1988, Chemotherapy for prostate carcinoma. In: Wittes, R. E., ed. *Consensus Development Conference on the Management of Clinically Localized Prostate Cancer.* NCI monographs No. 7 Washington D.C.: Government Printing Office: 151–153 (NIH publication no. 88–3005). Accordingly, there is a great demand for improved prostate cancer therapeutics.

2.2 CANCER IMMUNOTHERAPY

It is well established that the immune system can function to kill tumor cells, including both primary and metastatic cancer cells. Indeed, evidence that the immune system recognizes the presence of neoplastic cancerous cells is supported by the existence of infiltrating lymphocytes in tumor tissues (Haskill et al., 1978, Contemp. Top. Immunobiol. 8: 107–170; Vose and Moore, 1985, Semin. Hematol. 22: 27–40). Yet, for reasons that have not been completely clear, despite the presence of immune cells, tumors often prevail and not only survive but metastasize to distant sites with unrestricted growth.

Recent advances in the understanding of T cell activation and recognition of target cells have begun to permit some progress in development of T cell mediated cancer immunotherapy (Schwartz, 1992, Cell 71: 1065–1068; Pardoll, 1992, Curr. Opin. Immunol. 4: 619–623).

In its most general form, the generation of an immune response begins with the sensitization of helper ($T_H$, CD4$^+$) and cytotoxic (CD8$^+$) T cell subsets through their interaction with antigen presenting cells (APC) that express major histocompatibility (MHC)-class I or class II molecules associated with antigenic fragments (i.e., specific amino acid sequences derived from the antigen which bind to MHC I and MHC II for presentation on the cell surface). The sensitized or primed CD4$^+$ T cells produce lymphokines that participate in the activation of B cells as well as various T cell subsets. The sensitized CD8$^+$ T cells increase in numbers in response to lymphokines and are capable of destroying any cells that express the specific antigenic fragments associated with matching MHC-encoded class I molecules. Thus, in the course of a cancerous tumor, CTL eradicate cells expressing cancer associated or cancer specific antigens, thereby limiting the progression of tumor spread and disease development.

Various methods for immunotherapy of a number of particular cancers have been suggested; however, to date no one has developed any therapeutic method that successfully elicits an effective immunotherapeutic response against primary or metastatic prostate cancer.

2.3 DENDRITIC CELLS FOR ANTIGEN PRESENTATION

Antigen presenting cells (APC) are particularly important in eliciting an effective immune response.

By definition, APC not only can present antigens to T cells with antigen-specific receptors, but can provide all the signals necessary for T cell activation. Such signals are incompletely defined, but probably involve a variety of cell surface molecules as well as cytokines or growth factors. Further, the factors necessary for the activation of naive or unprimed T cells may be different from those required for the re-activation of previously primed memory T cells. The ability of APC to both present antigens and deliver signals for T cell activation is commonly referred to as an accessory cell function. Although monocytes and B cells have been shown to be competent APC, their antigen presenting capacities in vitro appear to be limited to the re-activation of previously sensitized T cells. Hence, they are not capable of directly activating functionally naive or unprimed T cell populations.

The term "dendritic cells" refers to a diverse population of morphologically similar cell types found in a variety of lymphoid and non-lymphoid tissues (Steinman, 1991, Ann. Rev. Immunol. 9: 271–296). These cells include lymphoid DC of the spleen, Langerhans cells of the epidermis, and veiled cells in the blood circulation. Although they are collectively classified as a group based on their morphology, high levels of surface MHC-class II expression, and absence of certain other surface markers expressed on T cells, B cells, monocytes, and natural killer cells, it is presently not known whether they derive from a common precursor or can all function as APC in the same manner.

Recent studies have described methods for the isolation and expansion of human DC's, including, from human peripheral blood. |Macatonia et al., 1991, Immunol. 74: 399–406; O'Doherty et al., 1993, J. Exp. Med. 178: 1067–1078 (isolation); and Markowicz et al., 1990, J. Clin. Invest. 85: 955–961; Romani et al., 1994, J. Exp. Med. 180: 83–93; Sallusto et al., 1994, J. Exp. Med. 179: 1109–1118; Berhard et al., 1995, J. Exp. Med. 55: 1099–1104

(expansion)]. PCT Publication WO 94/02156 describes a method for isolating human DC's to present antigens to induce antigen specific T cell-mediated responses. Adoptive cellular immunotherapy and use of the DC's against infectious diseases and cancer are mentioned.

Citation or identification of any reference in Section 2 (or any other section) of this application shall not be construed as an admission that such reference is available as prior art to the present invention.

3. SUMMARY OF THE INVENTION

The present invention provides methods, and compositions, for use of dendritic cells to activate T cells for immunotherapeutic responses against primary or metastatic prostate cancer. The DC's obtained from human donors, after exposure to a prostate cancer antigen or antigenic fragment, are administered to a prostate cancer patient to activate the relevant T cell responses in vivo. Alternatively, the DC's are exposed to a prostate cancer antigen in vitro and incubated with primed or unprimed T cells to activate the relevant T cell responses in vitro. The activated T cells are then administered to a prostate cancer patient. In either case, the DC's are advantageously used to elicit an immunotherapeutic growth inhibiting response against a primary or metastatic prostate tumor.

In one embodiment, the invention provides a method for producing a cancer growth inhibiting response, which comprises administering, to a prostate cancer patient in need thereof, an effective amount of activated T cells, in which the T cells were activated in vitro by exposure to human dendritic cells exposed to a prostate cancer antigen. In another embodiment, the invention provides a method for producing a cancer growth inhibiting response, which comprises administering, to a prostate cancer patient in need thereof, an effective amount of human dendritic cells, exposed in vitro to a prostate cancer antigen, such that after administration the human dendritic cells elicit an immune response or augment an existing immune response against the prostate cancer.

Prostate cancer antigens useful for the methods and compositions of the invention include but are not limited to: a lysate of LNCAP cells, a membrane preparation of LNCAP cells, a lysate of prostate tumor cells of a prostate cancer patient, a membrane preparation of prostate tumor cells of a prostate cancer patient, purified prostate specific membrane antigen (PSMA), a peptide having the amino acid sequence LLHETDSAV, a peptide having the amino acid sequence LHETDSAV, a peptide having the amino acid sequence LXXXXXXV where X represents any amino acid, purified prostate specific antigen (PSA), and a purified prostate mucin antigen recognized by monoclonal antibody PD41.

The present invention, further provides compositions comprising isolated human dendritic cells exposed to a prostate cancer antigen(s), as well as cryopreserved isolated human dendritic cells and extended life span human dendritic cells which are useful for eliciting immunotherapeutic responses against primary and/or metastatic prostate cancer.

4. BRIEF DESCRIPTION OF THE FIGURES

The present invention may be more fully understood by reference to the following detailed description of the invention, examples of specific embodiments of the invention and the appended figures in which:

FIG. 1 represents histograms of results of flow cytometric analyses of cultured dendritic cells which illustrate the expressed cell surface antigens. The cells were cultured in the presence of GM-CSF and IL-4. The (topmost) upper left histogram represents background fluorescence staining using the secondary (2°) antibody, i.e., goat anti-mouse Ig, in the absence of any primary (1°) antibody. The rest of the histograms represent fluorescence staining in the presence of 2° antibody and each of the enumerated 1° antibodies, respectively, anti-CD1a, anti-CD3, anti-CD4, anti-CD11c, anti-CD14, anti-CD19, anti-B7/BB1 and anti-HLA-DR antibodies. See text Section 6 for details.

Figure 2:
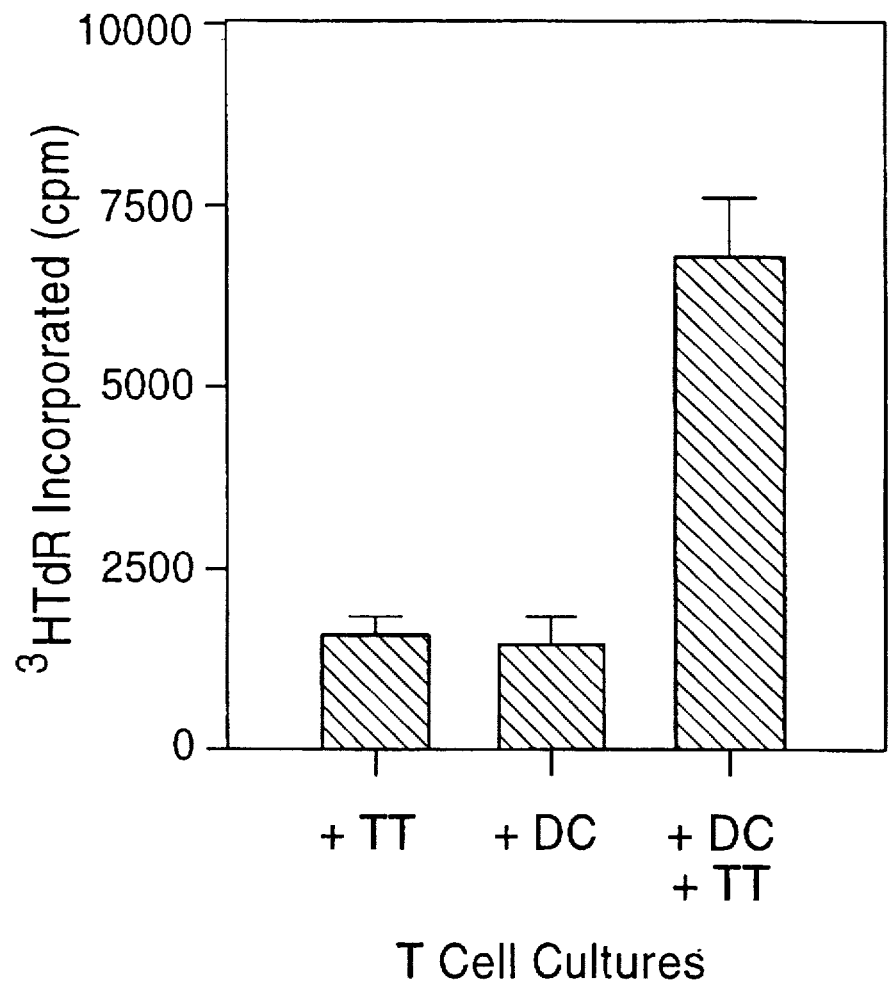

FIG. 2 graphically illustrates in vitro activation of T cells by tetanus toxoid (TT) presented by autologous DC's. See text Section 6 for details of the assays conducted in triplicate. The extent of T cell proliferation, represented by $^3$HTdR incorporated (cpm), is presented along the y axis. Three different culture conditions for the T cells are represented along the x axis: tetanus toxoid alone (+TT); dendritic cells alone (+DC); and tetanus toxoid with dendritic cells (+DC-TT). Individual standard deviations are shown.

Figure 3:
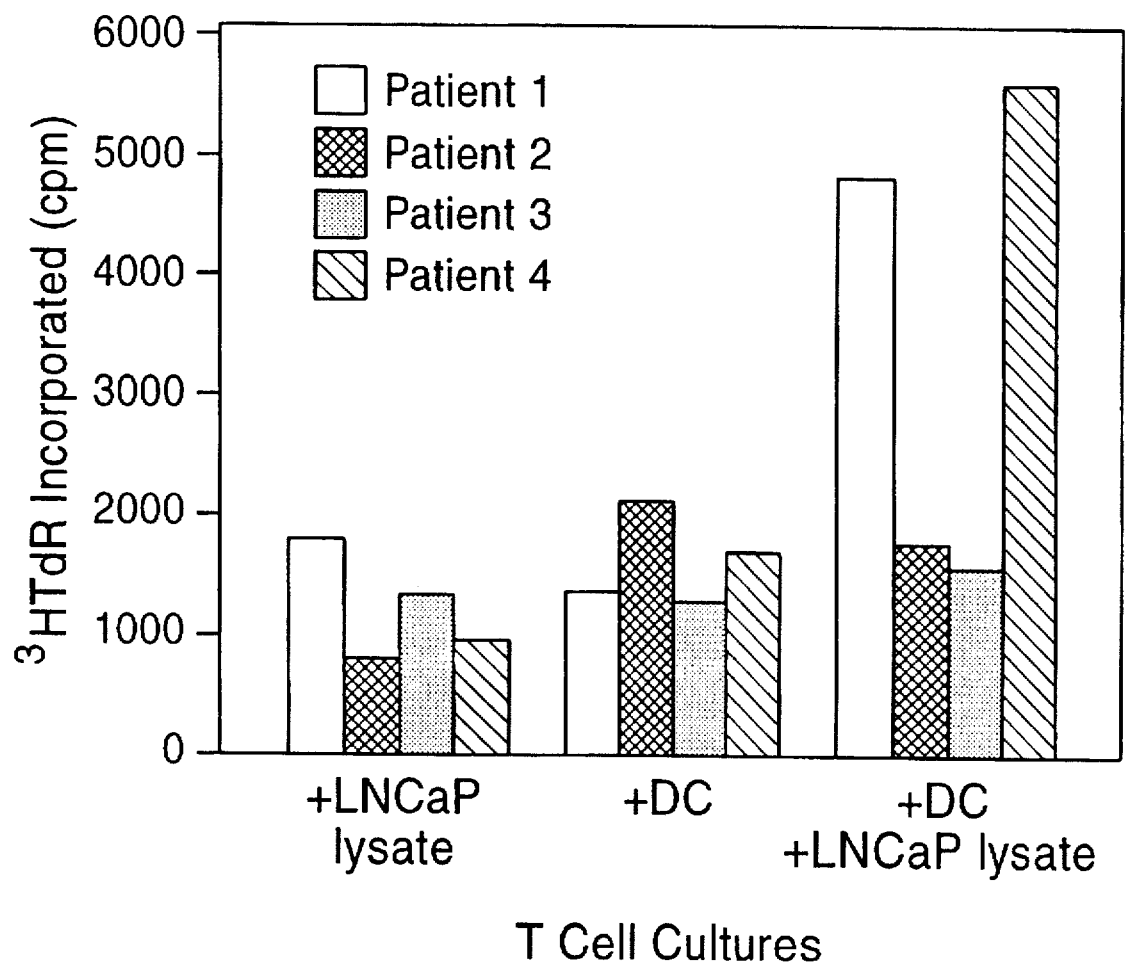

FIG. 3 graphically illustrates in vitro activation of T cells from four prostate cancer patients by presentation of prostate cancer antigen by autologous dendritic cells. Data from each individual patient is shown by different bar graph patterns as indicated. The extent of T cell proliferation, represented by $^3$H-Thymidine ($^3$HTdR) incorporated (cpm), is presented along the y axis. Three different culture conditions for the T cells are represented along the x axis: a prostate cancer antigen alone (+LNCaP lysate); dendritic cells alone (+DC); and a prostate cancer antigen with dendritic cells (+DC+ LNCAP lysate). See text Section 6.4. for details.

Figure 4:
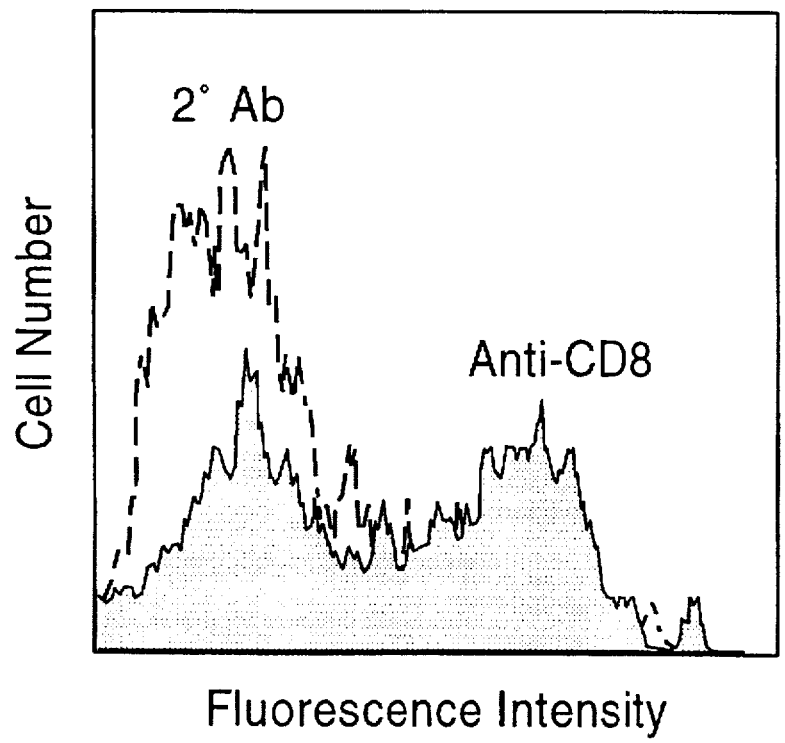

FIG. 4 is a histogram illustrating fluorescence flow cytometric analysis of the population of T cells proliferated in response to autologous DC presentation of LNCAP lysate as antigen. Background fluorescence represented by experiments with 2° antibody (goat anti-mouse Ig) alone is shown by the dotted line histogram. Fluorescence obtained in experiments using the 2° antibody with the 1 antibody (anti-CD8) antibody are shown by the solid line histogram. See text Section 6 for details.

Figure 5:
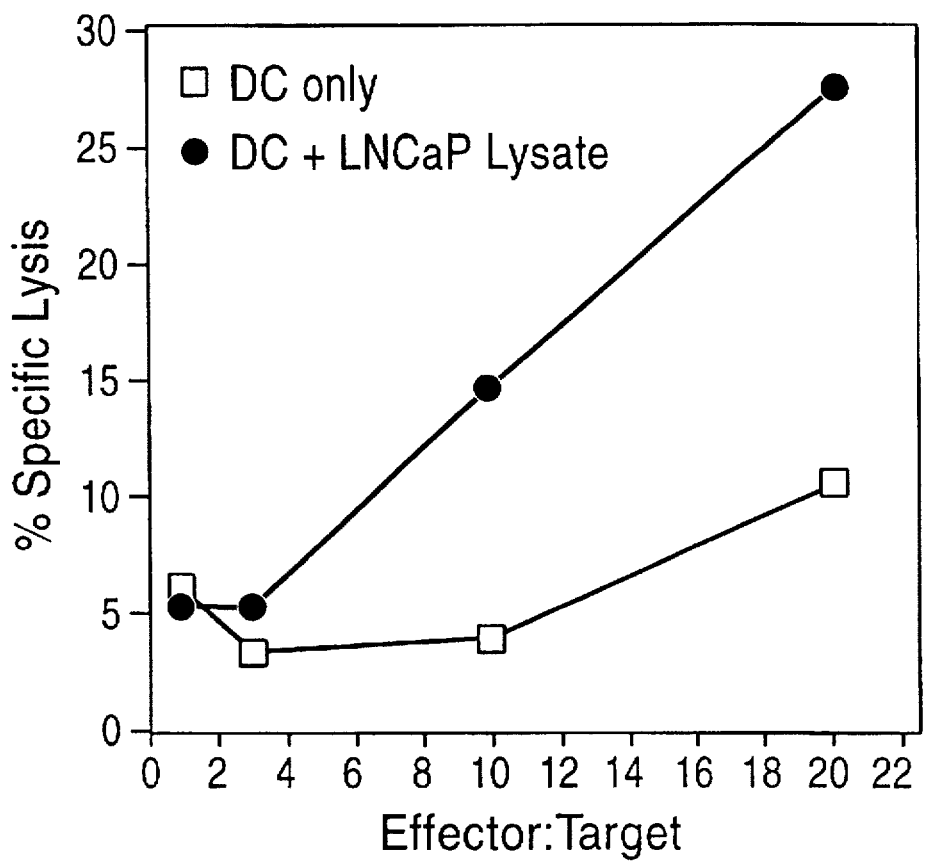
Figure 6:
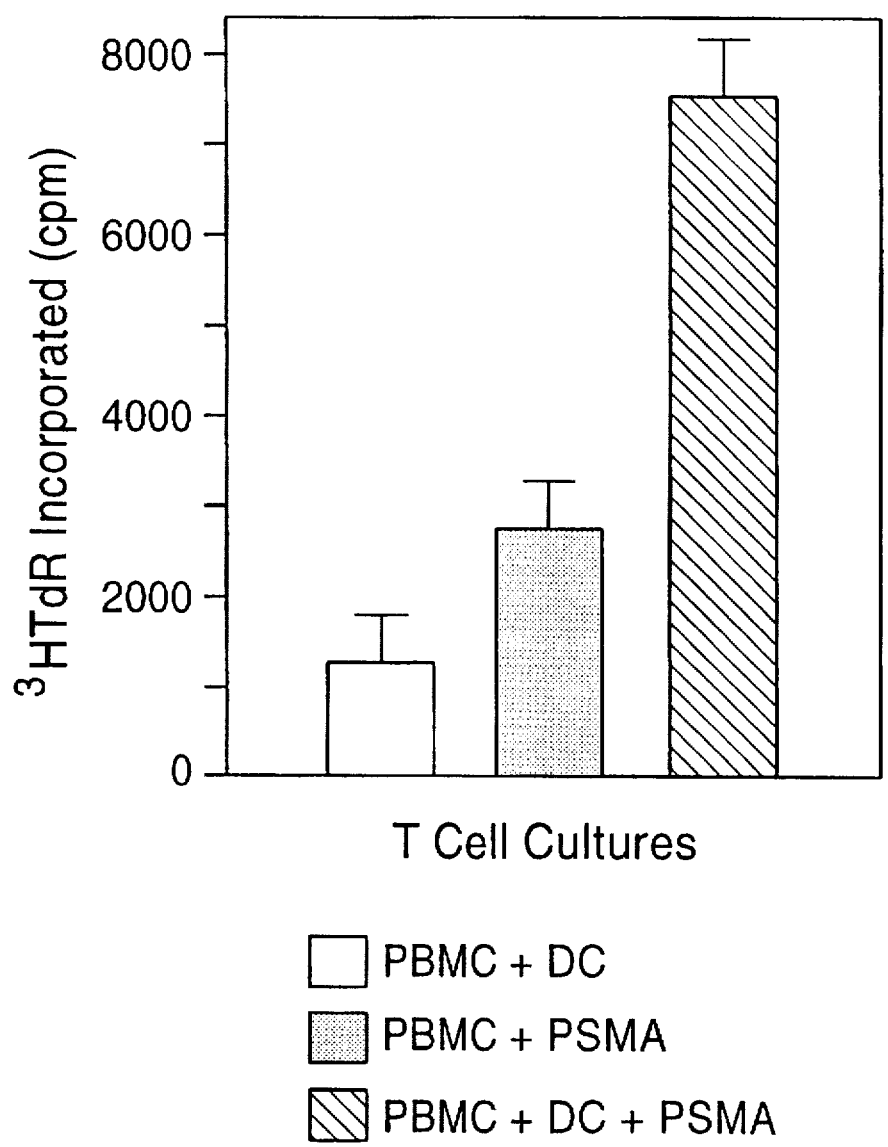

FIG. 5 graphically illustrates cytolytic activity of T cells stimulated, in vitro, in response to autologous DC presentation of LNCaP lysate as antigen. Average percent specific lysis of target cells is represented (y axis) as a function of (x axis) Effector (activated T cells): Target Cells (autologous DC's presenting LNCaP ◆ or autologous DC's alone ■). Experiments were performed in triplicate and the values presented represent the average; standard error of the mean for all experiments was <10%. See text Section 6.4 for details FIG. 6 illustrates in vitro activation of T cells (PBMC) by presentation of prostate cancer antigen by previously frozen autologous dendritic cells. The prostate cancer antigen used was purified prostate specific membrane antigen (PSMA). The extent of T cell proliferation, represented by $^3$H-TdR incorporated is shown along the y axis. Values are expressed as mean cpm±standard deviation (S.D.). Each experiment was conducted in 4 replicates. Three different culture conditions for the T cells are represented along the x axis: T cells plus dendritic cells (PBMC+DC); T cells plus PSMA alone (PBMC +PSMA); and T cells plus dendritic cells plus PSMA (PBMC+DC+PSMA). See text Section 7.1 for details.

Figure 7:
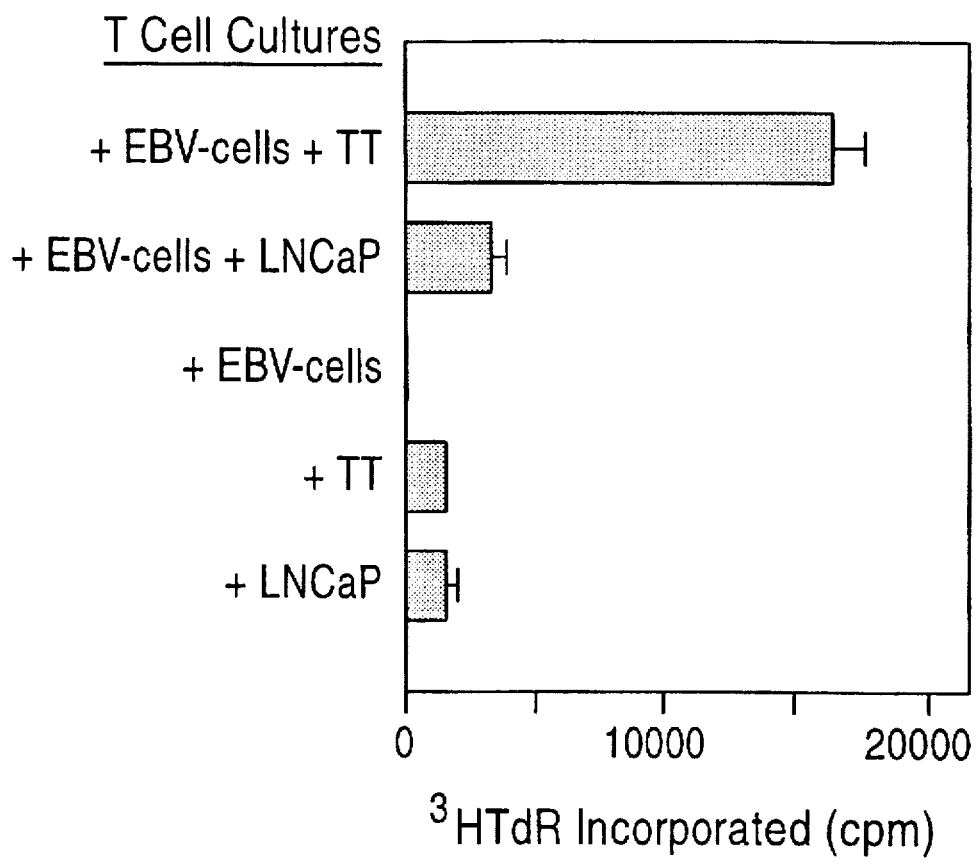

FIG. 7 illustrates in vitro activation of T cells by presentation of antigens by previously frozen autologous extended life span dendritic cells. The extent of T cell proliferation, represented by $^3$H-TdR incorporated is shown along the x axis. Values are expressed as mean value ±S.D. after subtraction of average background (PBMC+medium only). Five different cultures of T cells are represented along the y axis: T cells plus extended life span dendritic cells plus tetanus toxoid (+EBV-cells+TT); T cells plus extended life span dendritic cells plus prostate antigen (+EBV-cells +LNCaP); T cells plus extended life span dendritic cells plus no antigen (+EBV-cells); T cells plus tetanus toxoid alone (+TT); and T cells plus prostate antigen alone (+LNCaP). See text Section 8 for details.

Figure 8:
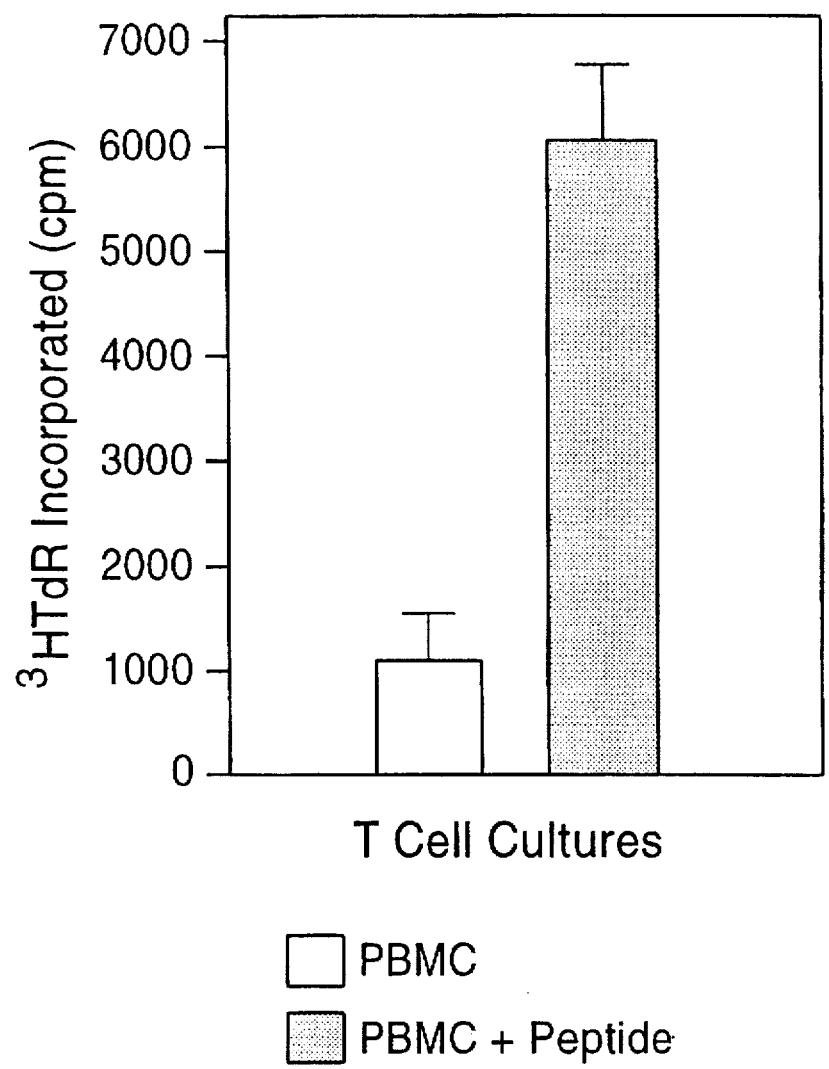

FIG. 8 illustrates that a peptide having amino acid sequence LLHETDSAV (comprising a portion of the amino acid sequence of PSMA) can stimulate proliferation of a mixed population of T cells (PBMC) obtained from peripheral blood of a prostate cancer patient. The extent of T cell proliferation, represented by $^3$HTdR incorporation (cpm), is presented along the y axis. See text Section 9 for details.

Figure 9:
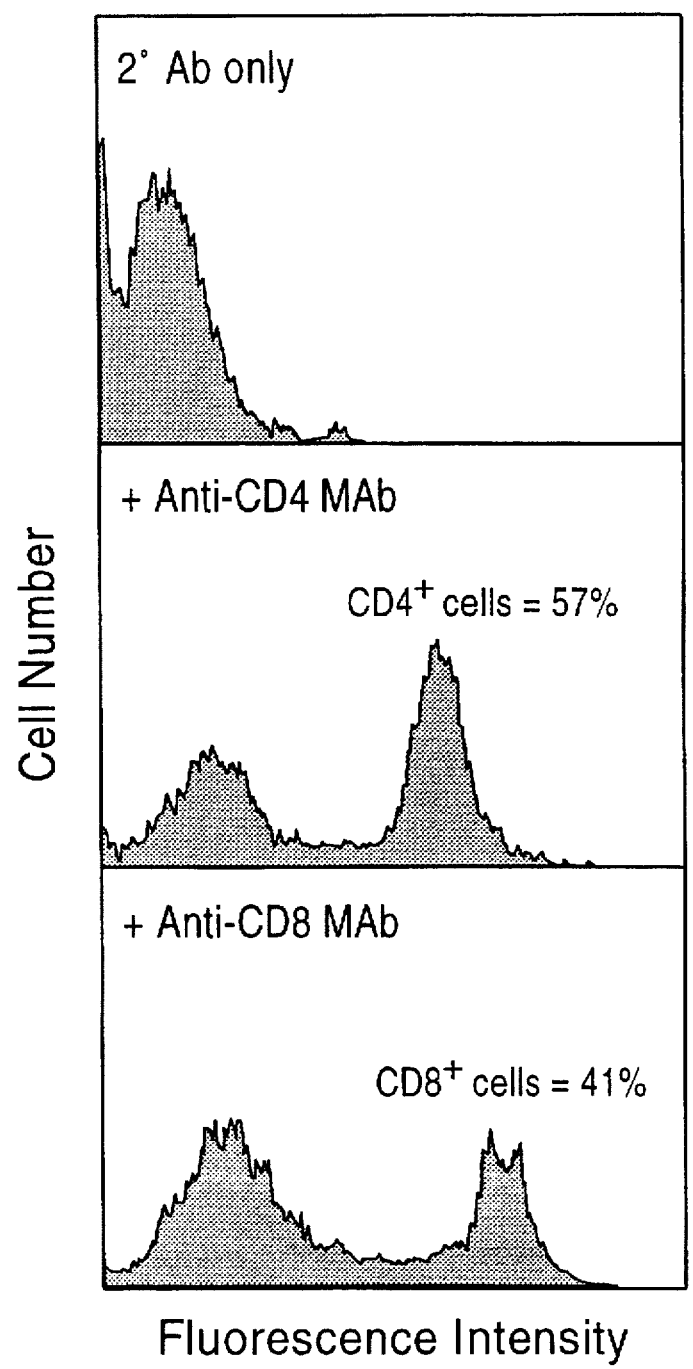

FIG. 9 (A–C) is a histogram illustrating fluorescence flow cytometric analysis of the population of T cells proliferated in response to the peptide LLHETDSAV as illustrated in FIG. 8. FIG. 9A illustrates background fluorescence obtained in experiments using 2° antibody only. FIG. 9B illustrates bound fluorescence obtained using the 2° antibody and anti-CD4 as the 1° antibody. FIG. 9C illustrates bound fluorescence obtained using 2° antibody and anti-CD8 as the 1° antibody. See text Section 9 for details.

5. DETAILED DESCRIPTION OF THE INVENTION

The present invention provides methods, and compositions, for use of dendritic cells to activate T cells for immunotherapeutic responses against primary or metastatic prostate cancer. The DC's obtained from human donors, once exposed to a prostate cancer antigen or specific antigenic peptide, are administered to a prostate cancer patient to activate the relevant T cell responses in vivo. Alternatively, the DC's are exposed to a prostate cancer antigen or specific antigenic peptide in vitro and incubated with primed or unprimed T cells to activate the relevant T cell responses in vitro. The activated T cells are then administered to a prostate cancer patient. In either case, the DC's are advantageously used to elicit an immunotherapeutic growth inhibiting response against a primary or metastatic prostate tumor.

Solely for ease of explanation, the description of the invention is divided into the following sections: (1) methods for obtaining or isolating dendritic cells, including DC's with extended lifespan or cryopreserved DC's; (2) prostate specific antigens for presentation by DC's; and (3) applications or methods of use of DC's to stimulate T cells against prostate cancer in vitro and in vivo.

5.1. ISOLATION OF DENDRITIC CELLS

Human DC's are obtained from any tissue where they reside including non-lymphoid tissues such as the epidermis of the skin (Langerhans cells) and lymphoid tissues such as the spleen, bone marrow, lymph nodes and thymus as well as the circulatory system including blood (blood DC's) and lymph (veiled cells). Human peripheral blood is an easily accessible ready source of human DC's and is used as a source according to a preferred embodiment of the invention. Cord blood is another source of human DC's and in cases where a male is born into a family known to be at high risk for prostate cancer, cord blood can be used as a source of DC's which can be cryopreserved for later use, if needed.

Because DC's occur in low numbers in any tissues in which they reside, including human peripheral blood, DC's must be enriched or isolated for use. Any of a number of procedures entailing repetitive density gradient separation, positive selection, negative selection or a combination thereof are used to obtain enriched populations or isolated DC's. Examples of such methods for isolating DC's from human peripheral blood include: O'Doherty et al, 1993, J. Exp. Med. 178: 1067–1078; Young and Steinman, 1990, J. Exp. Med. 171: 1315–1332; Freudenthal and Steinman, 1990, PNAS USA 57: 7698–7702; Macatonia et al., 1989, Immunol. 67: 285–289; and Markowicz and Engleman, 1990, J. Clin. Invest. 85: 955–961. A method for isolating DC's from human peripheral blood which avoids exposure of the cells to sheep red blood cells and/or fetal calf serum is described in PCT Publication WO94/02156. An example of a method for isolating DC's from lymphoid tissue is described in Macatonia et al., 1989, J. Exp. Med. 169: 1255–1264.

Once the DC's are obtained, they are cultured in appropriate culture medium to expand the cell population and/or maintain the DC's in a state for optimal antigen uptake, processing and presentation. Particularly advantageous for maintenance of the proper state of "maturity" of DC's in in vitro culture is the presence of both granulocyte/macrophage colony stimulating factor (GM-CSF) and interleukin 4 (IL-4). Preferred is a combination of GM-CSF : IL-4 in concentration of about 500 units/ml of each. A recent study reveals optimal antigen presentation by "immature" vs. mature DC (Koch et al., 1995, J. Immunol. 155: 93–100). Immature DC's may be preferred according to certain embodiments of the present invention.

As illustrated in the examples, infra, in Section 6, human DC's were isolated from peripheral blood of prostate cancer patients, and after about 7 days in culture, about 20–50 fold higher numbers of DC's competent and able to activate prostate antigen specific T cells were recovered compared to those directly isolated from peripheral blood.

According to a preferred embodiment of the invention, DC's are obtained from a prostate cancer patient to be treated. The DC's are used to activate autologous T cells of the patient, either in vitro or in vivo, for cancer immunotherapy and/or tumor growth inhibition.

According to an alternate embodiment, DC's are obtained from a healthy individual known not to be suffering from prostate cancer. The relevant HLA antigens (both class I and II, e.g., HLA-A, B, C and DR) on the individual's PBMC's are identified and DC's which match the prostate cancer patient, in terms of HLA antigens, are isolated and expanded as described above. For example, in certain instances, a late stage prostate cancer patient who has been treated with radiation and/or chemotherapy agents often are not able to provide sufficient or efficient DC's. Thus, DC's from healthy HLA-matched individuals, such as siblings, can be obtained and expanded using any of the methods described above and incubated in vitro with a prostate cancer antigen to elicit activated T cells for immunotherapy and/or tumor growth inhibition in the HLA-matched prostate cancer patient.

According to another embodiment of the invention, "extended life span dendritic cells" are used. Human cells have a finite life span in vitro usually limited to approximately 50–70 population doublings before undergoing apoptosis. As used herein, the term "extended life span dendritic cells" is intended to mean DC's that have been genetically modified so that they can be expanded in in vitro cell culture medium for an extended period of time, including but not limited to at least about 100 additional population doublings. Extended life span DC's are obtained, for example, by EBV-transformation of DC's obtained from peripheral blood of prostate cancer patients, or by insertion into DC's, using techniques known to those skilled in the art, of a specific cell cycle regulatory gene including but not limited to a gene which encodes cyclin A, B, D or E or retinoblastoma protein.

As illustrated in the examples, infra in Section 8, extended life span DC's have been obtained by EBV transformation of a population of isolated DC's. A number of clones have been obtained which express the relevant DC characteristic antigens and continue to grow and divide well after normal isolated DC's do not.

According to yet another embodiment of the invention, DC's can be preserved, e.g., by cryopreservation either before exposure or following exposure to a prostate cancer antigen.

Cryopreservation agents which can be used include but are not limited to dimethyl sulfoxide (DSO) (Lovelock and Bishop, 1959, Nature 183: 1394–1395; Ashwood-Smith, 1961, Nature 190: 1204–1205), glycerol, polyvinylpyrrolidone (Rinfret, 1960, nn. N.Y. Acad. Sci. 85: 576), polyethylene glycol (Sloviter and Ravdin, 1962, Nature 196: 548), albumin, dextran, sucrose, ethylene glycol, i-erythritol, D-ribitol, D-mannitol (Rowe et al., 1962, Fed. Proc. 21: 157), D-sorbitol, i-inositol, D-lactose, choline chloride (Bender et al., 1960, J. Appl. Physiol. 11520), amino acids (Phan The Tran and Bender, 1960, Exp. Cell Res. 20: 651), methanol, acetamide, glycerol monoacetate (Lovelock, 1954, Biochem. J. 56: 265), and inorganic salts (Phan The Tran and Bender, 1960, Proc. Soc. Exp. Biol. Med. 104: 388; Phan The Tran and Bender, 1961, in Radiobiology, Proceedings of the Third Australian Conference on Radiobiology, Ilbery, P. L. T., ed., Butterworth, London, p. 59).

A controlled slow cooling rate is critical. Different cryoprotective agents (Rapatz et al., 1968, Cryobiology 5(1): 18–25) and different cell types have different optimal cooling rates (see, e.g., Rowe and Rinfret, 1962, Blood 20: 636; Rowe, 1966, Cryobiology 3(1): 12–18; Lewis et al., 1967, Transfusion 7(1):17–32; and Mazur, 1970, Science 168939–949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of hematopoietic stem cells, particularly from bone marrow or peripheral blood, is largely applicable to the DC's of the invention. Such a discussion can be found, for example, in the following references, incorporated by reference herein: Gorin, 1986, Clinics in Haematology 15(1)"19–48; Bone-Marrow Conservation, Culture and Transplantation, Proceedings of a Panel, Moscow, Jul. 22–26, 1968, International Atomic Energy Agency, Vienna, pp. 107–186.

Other methods of cryopreservation of viable cells, or modifications thereof, are available and envisioned for use (e.g., cold metal-mirror techniques; Livesey and Linner, 1987, Nature 327: 255; Linner et al., 1986, J. Histochem. Cytochem. 34(9): 1123–1135; see also U.S. Pat. No. 4,199, 022 by Senken et al., U.S. Pat. No. 3,753,357 by Schwartz, U.S. Pat. No. 4,559,298 by Fahy.

Frozen cells are preferably thawed quickly (e.g., in a water bath maintained at 37°–41° C.) and chilled immediately upon thawing.

It may be desirable to treat the cells in order to prevent cellular clumping upon thawing. To prevent clumping, various procedures can be used, including but not limited to the addition before and/or after freezing of Dnase (Spitzer et al., 1980, Cancer 45: 3075–3085), low molecular weight dextran and citrate, hydroxyethyl starch (Stiff et al., 1983, Cryobiology 20: 17–24), etc.

The cryoprotective agent, if toxic in humans, should be removed prior to therapeutic use of the thawed DC's.

One way in which to remove the cryoprotective agent is by dilution to an insignificant concentration.

Once frozen DC's have been thawed and recovered, they are used to activate T cells as described above with respect to non-frozen DC's.

As illustrated in the examples infra, in Section 8, extended life span DC's have been cryopreserved, thawed and used to present antigen to activate T cells in vitro.

5.2 PROSTATE SPECIFIC ANTIGENS FOR PRESENTATION BY DENDRITIC CELLS

A number of antigens or antigenic compositions are useful, according to the present invention, for presentation by the DC's to activate T cells for prostate immunotherapeutics.

According to one embodiment, a lysate of LNCaP, a prostate cancer cell line, first described by Horoszewicz et al., 1980, Prog. Clin. Biol. Res. 37: 115–132; 1983, Cancer Res. 43: 1809–1818, is used as antigen presented by the DC's. A crude cell lysate obtained simply by repetitive freezing and thawing of LNCAP cells can be used as antigen. An illustrative example of the use of this antigen is presented in Section 6, infra. Alternatively, a membrane preparation of LNCaP cells, as described by Horoszewicz et al., 1987, Anticancer Res. 7: 927–936, can be used.

According to another embodiment, a prostate tumor cell lysate recovered from surgical specimens can be used as antigen. For example, a sample of a cancer patient's own tumor, obtained at biopsy or at surgical resection, can be used to provide a cell lysate for antigen. Alternatively, a membrane preparation of tumor cells of a prostate cancer patient can be used as antigen.

According to another embodiment, purified prostate specific membrane antigen (PSMA, also known as CYPP antigen), which specifically reacts with monoclonal antibody 7Ell-C.5 [(see generally Horoszewicz et al., 1987, supra, U.S. Pat. No. 5,162,504; Feng et al., 1991, Proc. Am. Assoc. Cancer Res. 32:(Abs. 1418):238)] can be used as antigen. Cloning of the gene encoding the PSMA antigen has been described by Israeli et al., 1994, Cancer Res. 54: 1807–1811. Expression of the cloned gene, e.g., in yeast cells, in a baculovirus expression system or in a mammalian cell culture expression system, will provide a ready source of the PSMA antigen for use according to the present invention.

According to another embodiment, an antigenic peptide having the amino acid sequence LLHETDSAV which corresponds to amino acid residues 4–12 PSMA can be used as antigen. According to another embodiment, an antigenic peptide having the amino acid sequence LHETDSAV which corresponds to amino acid residues 712–179 of PSMA can be used as antigen.

According to another embodiment, an antigenic peptide having an amino acid sequence LXXXXXXV where X represents any amino acid residue can be used as antigen.

According to yet another embodiment, prostate specific antigen (PSA) (see Papsidero et al., 1980, Cancer Res. 40: 2428–2432; McCormack et al., 1995, Urology 45(5): 729–744 can be used as antigen.

According to still another embodiment, a prostate mucin antigen, recognized by monoclonal antibody PD41, described by Wright (U.S. Pat. No. 5,227,471 and U.S. Pat. No. 5,314,996; Beckett et al., 1991, Cancer Res. 51: 1326–1333) can be used as antigen. Alternatively, a crude lysate of prostate tumor cells which bind to the antibody produced by the hybridoma cell line (ATCC HB 11094) and which express the PD41 mucin antigen could be used as antigen.

According to the present invention, DC's can be exposed to a desired prostate cancer antigen or antigenic composition by incubating the DC's with the antigen in in vitro culture medium. In one mode, the antigen, in aqueous soluble or aqueous suspension form, is added to cell culture medium at the same time as the DC's and T cells to be stimulated are added. See Section 6, infra, for an illustrative example of this method. As demonstrated in Section 6, the DC's advantageously took up antigen for successful presentation to T cells. In another mode, antigens are introduced to the cytosol of the DC's by alternate methods, including but not limited to osmotic lysis of pinocytic vesicles and the use of pH sensitive liposomes, etc. See, generally, Okada et al., 1982, "Introduction of Macromolecules Into Cultured mammalian Cells by Osmotic Lysis of Pinocytic Vesicles", Cell 29: 33; Poste et al., 1976, "Lipid Vesicles as Carriers for Introducing Biologically Active Materials Into Cells", Methods Cell Biol. 14: 33; Reddy et al., 1991, "pH Sensitive Liposomes Provide an Efficient Means of Sensitizing Target Cells to Class I Restricted CTL Recognitition of a Soluble Protein", J. Immunol. Methods 141: 157.

5.3 APPLICATIONS OR METHODS OF USE

5.3.1 USE OF DENDRITIC CELLS TO PRESENT PROSTATE ANTIGEN IN VITRO

As mentioned above, according to one embodiment of the invention, isolated human DC's, exposed to a prostate specific antigen by any of the methods described above in Section 5.2, are used to activate T cells in vitro against prostate cancer. The DC's can be used immediately after exposure to antigen to stimulate T cells. Alternatively, the DC's can be maintained in the presence of a combination of GM-CS and IL-4 prior to simultaneous exposure to antigen and T cells.

T cells or a subset of T cells can be obtained from various lymphoid tissues for use as responder cells. Such tissues include but are not limited to spleens, lymph nodes, and peripheral blood. The cells can be co-cultured with DC exposed to antigen as a mixed T cell population or as a purified T cell subset.

For example, it may be desired to culture purified CD8$^+$ T cells with antigen exposed DC's to elicit prostate specific CTL. In addition, early elimination of CD4$^+$ T cells may prevent the overgrowth of CD4$^+$ cells in a mixed culture of both CD8$^+$ and CD4$^+$ T cells. T cell purification may be achieved by positive, or negative selection, including but not limited to, the use of antibodies directed to CD2, CD3, CD4, CD5, and CD8.

On the other hand, it may be desired to use a mixed population of CD4$^+$ and CD8$^+$ T cells to elicit a prostate specific response encompassing both a cytotoxic and T$_H$ immune response.

According to a preferred embodiment, the T cells are obtained from the same prostate cancer patient from which the DC's were obtained. After stimulation or activation in vitro, the autologous T cells are administered to the patient to provoke and afford an immunoresponse which slows or inhibits prostate tumor growth.

For example, T cells are administered, by intravenous infusion, at doses of about $10^8$–$10^9$ cells/m$^2$ of body surface area (see, Ridell et al., 1992, Science 257: 238–241). Infusion can be repeated at desired intervals, for example, monthly. Recipients are monitored during and after T cell infusions for any evidence of adverse effects.

According to another embodiment, the T cells are obtained from a prostate cancer patient and the DC's which are used to stimulate the cells are obtained from an HLA-matched healthy donor. According to yet another embodiment, both the T cells and the DC's are obtained from an HLA-matched healthy donor, e.g., a sibling of the prostate cancer patient. This embodiment may be particularly advantageous, for example, when the patient is a late stage prostate cancer patient who has been treated with radiation and/or chemotherapy agents and may not be able to provide sufficient or efficient DC's. The T cells after stimulation, are administered as described above.

5.3.2 USE OF DENDRITIC CELLS TO PRESENT PROSTATE ANTIGENS IN VIVO

According to another embodiment of the invention, DC's isolated from a prostate cancer patient are cultured, exposed in vitro to a prostate cancer antigen and after expansion and/or cryopreservation are administered back to the patient to stimulate an immune response, including T cell activation, against the patient's cancer cells in vivo. Using this approach with the patient's own dendritic cells provides the following advantages: (1) no foreign DNA is utilized; (2) infection of cells for purposes of cDNA expression using various viral vectors are eliminated; (3) antigen is presented to dendritic cells in the form of soluble protein which will be taken into the dendritic cells and processed for MHC/peptide presentation of the cell surface; (4) dendritic cells express B7's on their surface alleviating the necessity to transfect this cDNA into dendritic cells; (5) the use of endogenous B7's on dendritic cell surface eliminates the need to provide T cells with Il-2 or other cytokines either in the form of the cytokine itself or transfection of the cDNA into specific cells; (6) all procedures are carried out using the patient's own cells.

In practice, DC's obtained as described above in Section 5.1, are exposed in vitro to a prostate cancer antigen, washed and administered to elicit an immune response or to augment an existing, albeit weak, response. As such, the DC's constitute an anti-prostate cancer vaccine and/or immunotherapeutic agent. DC's presenting a prostate specific antigen are administered, via intravenous infusion, at a dose of about $10^6$–$10^8$ cells. The immune response of the patient can be monitored. Infusion can be repeated at desired intervals based upon the patient's immune response.

The following examples are presented for purposes of illustration only and are not intended to limit the scope of the invention in any way.

6. EXAMPLE: USE OF DENDRITIC CELLS TO STIMULATE PROSTATE SPECIFIC T CELLS

The following example demonstrates that human dendritic cells, obtained from prostate cancer patients, were able to elicit the proliferation of both helper and cytolytic T cells.

6.1. MATERIALS AND METHODS

6.1.1. CELL LINES AND REAGENTS

LNCAP, a prostate cancer cell line, Horoszewicz et al., 1983, LNCAP Model of Human Prostatic Carcinoma, Cancer Research, 43: 1809–1818, (CRL 1740, ATCC, Rockville, Md.), was maintained in culture in RPMI 1640. Granulocyte/macrophage colony stimulating factor (GM-CSF), recombinant human interleukin 2 (IL2) and interleukin 4 (IL4) were generous gifts from Amgen (Thousand Oaks, Calif.). Monoclonal antibodies Leu-6 (anti-CD1a), Leu-4 (anti-CD3), Leu-3a (anti-CD4), Leu-2a (anti-CD8), Leu-M3 (anti-CD14), anti-HLA-DR (MHC Class II), and BB1 (anti-B7/BB1) were purchased from Becton-Dickinson, San Jose, Calif. Monoclonal antibodies S125-C1 (anti-CD 19) and 3.9 (anti-CD1 lc) were purchased from Sigma, St. Louis, Mo.

6.1.2. PROSTATE CANCER PATIENTS

Patients with a histologic confirmation of prostatic cancer were selected for this study which included a signed informed consent. Fifty cc of heparinized peripheral blood were drawn every 2 weeks during the period of observation which continues. Details regarding clinical stage, hematologic status, and other relevant treatments are recorded in Table 1. The American Urological System of staging was employed, i.e., $B_2$=tumor confined to the prostate in both lobes, $C_2$=large locally invasive tumor, $D_1$=positive pelvic lymph node, $D_2$=metastatic disease.

TABLE 1

Clinical Profiles of Dendritic Cell Donors

| Patient | Age | Clinical Stage | Hormonal Status | Bone Marrow Status | Hematocrit (Vol %) | Platelets <100,000/mm³ | Average PBMC yield# × 1000 | DC yield* |
|---|---|---|---|---|---|---|---|---|
| 1 | 64 | $D_1$ | Hormone Refractory, Leupron + Flutamide | Intact | 45 | 0 | 1000 | 8–12% |
| 2 | 71 | $D_2$ | Hormone Refractory, Post-Orchiectomy | Impaired Ext. Radiation, $2 \times Sr^{89}$ | 34 | + | 100 | 4–10% |
| 3 | 68 | $C_2$ | Hormone Refractory, Post-Orchiectomy | Ext. Radiation | 46 | 0 | 1000 | 7–11% |
| 4 | 65 | $D_2$ | Hormone Refractory, Post-Orchiectomy | Ext. radiation | 33 | 0 | 1000 | 10–14% |
| 5 | 75 | $B_2$ | Non-Treated | Intact | 47 | 0 | 1000 | 10–13% |
| 6 | 70 | $D_2$ | Hormone Refractory, Post-Orchiectomy | Impaired, Ext. Radiation, Multiple Sites, $1 \times Sr^{89}$ | 25 | + | 100 | 2–8% |
| 7 | 80 | $D_2$ | Hormone Refractory, Post-Orchiectomy | Ext. Radiation, Multiple Sites | 29 | + | 1000 | 5–10% |
| 8 | 69 | $D_1$ | Hormone Refractory, Post-Orchiectomy $R_x$ Flutamide | Intact | 45 | 0 | 1000 | 8–11% |
| 9 | 62 | $D_2$ | Hormone Refractory, Post-Orchiectomy $R_x$ Emcyt | Impaired, Ext. Radiation, Multiple Sites, $1 \times Sr^{89}$ | 33 | 0 | 300 | 6–9% |
| 10 | 85 | $B_2$ | Intact | Intact | 46 | 0 | 900 | 9–13% |

The number of PBMC isolated from 1 ml of blood
*The number of DC cultured for 7 days/the starting number of PBMC × 100%. The average volume of blood drawn every session = 50 ml Most of these patients are in clinical stages $D_1$ or $D_2$, hormone refractory prostatic adenocarcinoma, and have undergone radiation therapy. Seven patients have undergone orchiectomy, among whom three have undergone $Sr^{89}$ therapy (patients 2, 6, and 9). Table 1 shows that peripheral blood mononuclear cells (PBMC) yields from these three patients were considerably lower ($1-3\times10^5$/cc) than those who were not given $Sr^{89}$ therapy ($10^6$/cc).

6.1.3. ISOLATION OF DENDRITIC CELLS

Peripheral blood was drawn from prostate cancer patients and was subjected to Lymphoprep (GIBCO-BRL, Gaithersburg, Md.) density gradient centrifugation. The peripheral blood mononuclear cells (PBMC) isolated were plated in 24 well plates ($10^6$–$10^7$ cells/well) and were incubated in a humidified incubator (37° C., 5% $Co_2$) for 90 minutes.

Non-adherent cells were removed with the supernatant and the wells are washed gently with warm (37° C.) OPTI-MEM medium (GIBCO-BRL, Gaithersburg, Md.) and 5% FCS. Dendritic cell propagation medium (DCPM: OPTI- MEM supplemented with 5% FCS, 500 units/ml GM-CSF and 500 units/ml IL-4) was added to the adherent cells (1 ml/well). These DC cells were cultured for 4–6 days before subculture 1:3 in DCPM.

The purity and identity of the isolated DC was confirmed by incubation with monoclonal antibodies anti-CD1a, -CD3, -CD4, -CD8, -CD11c, -CD14, -CD19, -HLA-DR and -B7/BB1 for 30 minutes on ice followed by a fluorescein-isothiocyanate labeled goat-anti-mouse Ig antibody for 30 minutes on ice. Fluorescence binding was analyzed using a FACS SCAN flow cytometer (Becton Dickinson, San Jose, Calif.). In other words, the cultured DC cells were harvested by pipetting (leaving behind highly adherent, bound macrophages) and were subjected to flow cytometer analyses for surface expression of different protein markers for cells of hematopoietic origin to confirm their DC identity. B7/BB1$^+$, CD11c$^+$, and HLA-DR$^+$ (MHC class II) but CD14$^-$, CD3$^-$ and CD19$^-$ confirms identity of the DC population.

6.1.4. T CELL PROLIFERATION ASSAYS

One million prostate cancer patients' PBMC were plated in microtiter plates in T cell media (TCM) consisting of RPMI 1640, HEPES, 2-mercaptoethanol, L-glutamine and penicillin-streptomycin, supplemented with 10% human AB serum (Sigma, St. Louis, Mo.) and 1U/ml recombinant human Il-2. Ten thousand mitomycin-C inactivated autologous DC and antigen was added to the well prior to culture.

The antigens used in these assays were: (1) tetanus toxoid at 500 ng/ml (TT; Sigma, St. Louis, Mo.); (2) the lysate of LNCAP cells from an equivalent of $10^5$ LNCAP cells/ml; or (3) purified PSMA. Lysate was prepared as described previously Topalian et al., 1994, Melanoma-Specific CD4+T Lymphocytes Recognize Human Melanoma Antigens Processed and Presented by Epstein-Barr Virus-Transformed B Cells, Int. J. Cancer 58: 69–79. Briefly, $10^7$ LNCaP in 1 ml phosphate buffer saline (PBS) was subjected to cycles of repeated freezing in liquid nitrogen and quick thawing in a 37° C. water bath. Purified PSMA was prepared as follows:

Preparation of the Protein-A 7E11-C5 column.

Protein-A agarose beads were washed with 10X volume 3M NaCl pH =9.0. The pH of the 2 ml of 7E1 1-C5 monoclonal antibody solution was adjusted to pH 9.0 and the NaCl concentration adjusted to 3M. Antibody solution and beads were mixed 1 hr at room temperature. After the incubation the beads were washed with 10X volume 3 M NaCl, 50 mM Sodium Borate. The beads were resuspended in 10X volumes 3M NaCl, 0.2M Sodium Borate, pH =9.0. Dimethylpimeladate was added to a concentration to 20 mM. The mixture was allowed to mix 30 minutes at room temperature. The reaction was stopped by washing the beads with 0.2M methanolamine pH 8.0. Then 0.2M ethanolamine pH 8.0 was added at 10X volume and the mixture was allowed to incubate with mixing for 2 hours. The final wash with 2X volume PBS 0.01 % merthiolate.

Immunoprecipitation of PSMA from Semen

Approximately 75 ml of human semen was collected from paid donors under the WHO guidelines for fertility testing. The semen was spun down at 10,000 RPMS for thirty minutes. The supernatant was then removed. The pellet was washed two times with PBS pH=7.4 then subjected to 1 ml of lysis buffer [1% Triton X-100, 50 mM HEPES 10% glycerol, 15 mM MgCl$_2$, 1 mM phenylmethylsulfonyl fluoride, and 1 mM ethylenebis(oxyethylenenitrilo) tetraacetic acid for one hour. The lysate was spun down at 10,000 RPMS for thirty minutes and the supernatant was collected.

The 7E1 1-C5 bound Protein-A beads were washed with 15 ml binding buffer (20 mM HEPES pH=7.5). After washing, the beads were added to 1 ml of the seminal pellet lysate and 2 ml of binding buffer. The mixture was allowed to incubate over night.

The next day the beads were washed with 15 ml binding buffer, followed by 10 ml of wash buffer (10 mM Sodium Phosphate). The elution buffer (100 mM Glycine pH=1.8) was added at 2 ml volumes and the fractions containing PSMA were collected.

The cell suspension was then added to a T cell proliferation assay. T cell cultures were incubated in a humidified 37° C. incubator supplemented with 5% CO$_2$ for 5 days prior to addition of 1 µCi $^3$H-Thymidine/well. After a 24 h incubation, cells were harvested in a semi-automatic cell harvester (Skatron, Stevina, Va.) and radioactivity of the collected cells was determined. T cell proliferation was assessed by measurement of average $^3$HTdR incorporation.

6.2. ISOLATION AND CHARACTERIZATION OF DENDRITIC CELLS FROM PROSTATE CANCER PATIENTS

DC were obtained from PBMC of prostate cancer patients as described in Section 6.1.3. above and cultured in DCPM as described. After 4–7 days in culture, clusters of dividing cells started to form and became less adherent to the tissue culture flask. These cells increased in size and showed a typical dendritic morphology (results not shown). In addition to these slightly adherent cells, tightly adherent macrophages were also present. The average number of cells with dendritic morphology obtained after a 7 day culture was 2–7×10$^6$ from 50 ml peripheral blood, representing 4–14% of the starting number of PBMC cultured (see Table 1).

In order to confirm the DC identity of the cultured cells, the cells were harvested by pipetting (leaving tightly bound macrophages behind) and were subjected to flow cytometric analyses for surface expression of different protein markers for cells of hematopoietic origin. Results are illustrated in FIG. 1.

As illustrated in FIG. 1, the cultured cells do not express lineage specific markers for T cells (CD3), B cells (CD19), or macrophages (CD14). CD1a, a marker for Langerhans cells (e.g., dendritic cells isolated from the skin), was expressed at a high level early in the culture, but the level decreased when the cells were maintained in culture for more than 14 days. CD11c (beta-2-integrin) and HLA-DR were expressed at high levels while B7/BB1 was expressed at moderate levels by these cells, confirming further the identify of the cultured cells as DC's.

These cultures ceased to expand after 2 passages, although the DC's maintained their characteristic morphology and surface antigen expression for up to one month when fed weekly with fresh dendritic cell propagation medium (DCPM).

6.3. STIMULATION OF ANTIGEN SPECIFIC T CELLS BY DENDRITIC CELLS

In order to assess the capacity of the cultured DC's to present antigen to and stimulate autologous T cells from the same patients, T cell proliferation assays were conducted as described above in Section 6.1.4. in triplicate. Tetanus toxoid (TT) was chosen as a representative antigen in these experiments to determine whether patients' memory T cells could be activated in vitro. Results are presented in FIG. 2.

FIG. 2 shows that autologous T cells cultured with the patients' DC's and TT proliferated at levels significantly higher than background levels (in the absence DC) and at levels significantly higher than T cells cultured with DC without TT, i.e., showing an autologous mixed lymphocyte reaction.

Thus, the results demonstrate that the presentation of TT by DC's is useful for T cell proliferation. More particularly, the results demonstrate that DC's obtained from prostate cancer patients are useful to activate antigen specific T cell proliferation.

6.4. STIMULATION OF PROSTATE SPECIFIC T CELLS BY DENDRITIC CELLS

The ability of DC's to present antigen specific for prostate cancer and stimulate autologous T cells of a prostate cancer patient was determined. In one study, a crude cellular lysate of LNCaP cells, a metastatic prostate cancer cell line, was used as a representative prostate cancer antigen in a T cell proliferation assay generally as described above in Section 6.1.4. Results are illustrated in FIG. 3.

FIG. 3 shows that significant increases in $^3$HTdR incorporation were observed in 2 of 4 cases when both DC's and LNCAP lysates were included in the T cell cultures. Thus, in 2/4 cases presentation of prostate specific antigen stimulated autologous T cell proliferation in vitro. It is our belief that the 2 negative cases with LNCaP lysate as antigen reflect the limitations of using a crude cellular lysate with variable concentration of prostate antigen. Additional experiments using purified prostate-specific membrane antigen (PSMA) support this view (results not shown).

In another experiment, T cells proliferated as a result of DC presentation of LNCaP lysate were expanded in culture, for 2 weeks, and subjected to fluorescence flow cytometric analysis to determine the representation of the two T cell subtypes, i.e., cytolytic T lymphocytes (CTL) and helper T cells ($T_H$) elicited. In particular, T cells proliferated as a result of DC presentation of LNCaP lysate were expanded, for two weeks, by culture in T cell propagation medium in the presence of mitomycin C-inactivated autologous DC and LNCAP lysate (equivalent to 104 LNCAP cell/ml). A 14 day old culture of T cells was harvested and analyzed for the expression of cytolytic T cell specific antigen; CD8, by fluorescence flow cytometry as described above. Results are illustrated in FIG. 4.

As demonstrated in FIG. 4, the CTL's (CD8+) represented about 40–50% of the T cells elicited against LNCaP by the DC presentation of LNCAP lysate. Thus, presentation of prostate antigen by autologous DC's is useful to elicit both cytolic (CTL's) and helper ($T_H$) T cells specific for prostate cancer.

In yet another experiment, T cells (both CD4$^+$ and CD8$^+$) activated as described above by DC's presenting LNCaP lysate as antigen demonstrated cytolytic activity using, as target cells, autologous DC's presenting LNCaP antigen.

Briefly, DC's were isolated from a prostate cancer patient, as described in Section 6.2 and were exposed to LNCAP lysate as described above. Autologous T cells were obtained as PBMC's and cultured in the presence of the LNCaP presenting DC's. T cells proliferated as a result of prostate antigen presentation by the DC's were expanded for a total of 21 days as described above.

The ability of the activated T cells to specifically lysis target cells was assessed using the CytoTox 96™ assay (Promega, Madison; Wis.). Briefly, effector cells (the 21 day T cells including both CD4$^+$ and CD8$^+$ cells) were incubated with 2×10$^4$ target cells in T cell propagation medium at effector: target cell ratios of 20:1, 10:1 and 3:1 for 5 hours at 37° C. in a $CO_2$ incubator. Target cells included: autologous DC's alone or autologous DC's exposed to LNCaP lysate |equivalent of 10$^5$ cells/ml (DC+LNCaP Lysate)| overnight. Released lactate dehydrogenase, a stable cytosolic enzyme that is released upon cell lysis was measured from culture supernatants with a coupled enzymatic assay which was monitored by reading absorbance at 490 mm. All experiments were performed in triplicate. Results are illustrated in FIG. 5.

As shown in FIG. 5, T cells proliferated as a result of prostate antigen presentation by DC's according to the present invention showed enhanced specific lytic activity against cells presenting the same prostate antigen. Thus, presentation of prostate antigen by DC's is useful to elicit T cells having specific cytolytic activity against cells expressing prostate antigen.

7. EXAMPLE: USE OF CRYOPRESERVED DENDRITIC CELLS TO STIMULATE PROSTATE SPECIFIC T CELLS

7.1. CRYOPRESERVED DENDRITIC CELLS FROM A PROSTATE CANCER PATIENT

Dendritic cells were isolated from PBMC of a prostate cancer patient as described above in Section 6 and cultured, as described above, in Section 6, for 7 days in the presence of 500 units/ml GM-CSF and IL-4.

On day 7, the isolated DC's were harvested and cryopreserved using 90% fetal calf serum and 10% dimethylsulfoxide. The cryopreserved DC's were stored frozen for a period of time, thawed in a 37° C. water bath and transferred to a 15 ml polypropylene tube and centrifuged at 1200 rpm for 5 min. The thawed DC's were then resuspended in medium containing 10% heat-inactivated human serum and counted.

One hundred thousand previously frozen T cells obtained from peripheral blood of the same prostate cancer patient (PBMC) were cultured in the presence or absence of 10$^4$ DC's together with 5 μl/well purified PSMA (see Section 6.1.4 above) in a total volume of 200 μl medium containing 10% heat-inactivated human serum and 1 unit/ml IL-2. One μCi/well $^3$H-Thymidine was added on day 6 and cultures were harvested 18 hours later. $^3$H-TdR incorporation was counted in a liquid scintillation counter. Each experiment was done in 4 replicates. Results are presented in FIG. 6. The average cpm and standard deviation are shown in the graph.

FIG. 6 demonstrates that a highly significant increase in $^3$HTdR incorporation was observed when both previously cryopreserved DC's and prostate specific antigen, i.e., PSMA, were included in the T cell cultures. Thus, presentation of prostate specific antigen by previously cryopreserved DC's stimulated autologous T cell proliferation in vitro. The effect was significantly greater than that observed with antigen alone or with DC's alone but no exogenous prostate antigen.

7.2. CRYOPRESERVED DENDRITIC CELLS OF NORMAL PATIENTS

PBMC are obtained from a normal or healthy individual known not to be suffering from prostate cancer. The PBMC are cross-typed and the relevant HLA antigens expressed noted. Relevant HLA antigens include such as HLA-A, B, C and DR. DC are isolated from the PBMC's as described in Section 6. The DC's are then cryopreserved as described in Section 7.1 above.

The cryopreserved DC are used according to the present invention to stimulate T cells in vitro, from a similarly matched HLA-typed individual or from a patient suffering from prostate cancer for use in the cancer patient.

7.3. ALTERNATE PROTOCOL FOR CRYOPRESERVATION AND USE OF DENDRITIC CELLS

Dendritic cells can be isolated from a prostate cancer patient or from a healthy donor, cryopreserved and used according to the methods of the invention as follows.

If desired, viable DC count, e.g., by trypan blue exclusion (Kucker, 1977, Biochemical Methods in Cell Culture and Virology, Dwoder, Hutchinsen & Ross, Stroudsburg, Pa., pp. 18–19) and manual cell counting can be performed.

The DC from the prostate cancer patient are cryopreserved using the following protocol:

1. Gently resuspend cells to a concentration of $4 \times 10^6$ viable cells/ml, using a mixture of cold (4° C.) 50% autologous plasma/RPMI-1640 or 50% heat-inactivated FCS/RPMI, and place the suspension on ice.
2. In a cryovial containing 1 ml of a chilled sterile cryoprotective medium of 20% DMSORPMI-1640, carefully layer a 1 ml portion of the above cell suspension on top of the cryoprotective medium.
3. Approximately 10 minutes prior to freezing, slowly invert the 1:1 mixture to promote mixing, then place it on ice to allow equilibrium between the cells and the cryoprotective medium. NOTE: The "layered" tube should not remain unfrozen for very long, so freezing should preferably be done within 20–30 minutes after exposure of cells to DMSO/RPMI solution.
4. Place the vials in a freezing rack, which in turn is placed in a 4° C. methanol bath, just deep enough to cover the cell suspension. This is then placed in the bottom (to ensure proper temperature) of a −80° C. freezer for at least 2 hours and less than 24 hours.
5. After cells reach the frozen state, carefully and quickly transfer them to a long term liquid nitrogen containment vessel. A cryogenic storage vessel which can be used is the LR 1000 refrigerator (Union Carbide Corp., Indianapolis, Ind.) which accommodates up to 40,000 cryules.

Following any desired length of time post-cryopreservation, the protocol below can be used to thaw the DC cells for use to stimulate autologous T cells specific to prostate cancer according to the present invention.

1. Remove vial of frozen cells from liquid nitrogen. Immediately the cell suspension by gently agitating the vial in a 37° C. water bath until just a small amount of ice remains.
2. Aseptically, begin to add drop-wise, a chilled mixture of 50% autologous serum/RPMI-1640 medium or 50% FCS/RPMI-1640 medium with a slight mixing between each drop, until the suspension volume is doubled.
3. Transfer this suspension to a larger centrifuge tube (12–15 ml) and continue to add, drop-wise, 50S serum/RPMI mixture with mixing between every other drop until the volume reaches 6–7 ml. Diluent may now be added, drop-wise, with mixing at every 0.5 ml increment until the volume reaches 9–10 ml. (NOTE: The reason for stepwise addition of diluent is to prevent osmotic shock to the cells as DMSO is diluted in the cell suspension).
4. Pellet cells by centrifugation at 4° C. 200 x g, for 10 minutes. Aspirate the supernatant.
5. Slowly add drop-wise 1 ml of chilled 20% autologous serum/RPMI-1640 mixture to the pellet. "Resuspend" the pellet by gently "flicking" the tube with a finger. After the pellet is resuspended (clumps may remain), resuspend it further by gently aspirating up and down with a 1 ml pipet.
6. Add an additional 4 ml chilled 20% autologous serum/RPMI, dropwise, with mixing between every drop; then add 0.5 ml as volume increases, as previously described.
7. Pellet cells by centrifugation at 4° C. 200xg, for 10 minutes. Aspirate the supernatant.
8. Resuspend with 2–5 ml of chilled 20% serum/RPMI mixture.
9. Perform cell counts (e.g., by use of a hemocytometer) and viability testing (e.g., by trypan blue exclusion).

Loss of cells due to clumping during the stepwise removal of DMSO can be diminished by including Dnase (20 U per $2 \times 10^6$ cells) or low molecular weight dextran and citrate (to reduce the Ph to 6.5).

8. EXAMPLE: USE OF EXTENDED LIFE SPAN DENDRITIC CELLS TO STIMULATE PROSTATE SPECIFIC T CELLS

Extended life span dendritic cells were prepared according to the present invention as follows:

DC's were isolated from human peripheral blood and cultured for 4–6 days as described above in Section 6.1.3. After 4–6 days in culture, in the presence of GM-CSF and IL-2, the DC's were infected with Epstein Barr Virus (EBV) generally as described by Walls & Crawford, in Lymphocytes: A Practical Approach, GCB Klaus, ed., IRL Press, Oxford, England, pp. 149–162. Briefly, DC's were harvested ($\sim 3$–$5 \times 10^6$ cells) and resuspended in a 5 ml B95-8 (an EBV-producing marmoset cell line, American Type Culture Collection, Rockville, Md.) culture supernatant. The cell suspension was transferred to a 25 cm$^2$ flask (Nunc, Inc., Naperville, Ill.) and incubated in a 37° C. CO$_2$ incubator for 24 hours. Five ml of fresh DCPM were added to the culture. Clusters of growing cells were observed 2–3 weeks post-infection. Extended life span DC cells were subcultured weekly, at 3–5 weeks post-infection.

The ability of the extended life span DC's to present antigen to stimulate autologous T cells of a prostate cancer patient was determined. In this study, either tetanus toxoid (TT) at 500 ng/ml or a lysate of LNCAP cells at an equivalent of $10^4$ cells/ml was used as representative antigen.

The autologous T cells used in the proliferation assay were obtained from peripheral blood and had been previously cryopreserved. One hundred thousand thawed T cells (designated "PBMC") were cultured in complete medium containing 10% heat-inactivated human serum and 1 unit/ml IL-2 as follows: in the presence of LNCaP antigen alone (+LNCaP); in the presence of TT antigen alone (+TT); in the presence of EBV-transformed DC's (+EBV cells); in the presence of EBV-transformed dendritic cells plus LNCAP antigen (+EBV-cells+LNCAP); or in the presence of EBV-transformed dendritic cells plus TT (+EBV-cells+TT). T cells in the presence of medium alone (PBMC+medium only) served as a background sample.

One μCi/well $^3$H-Thymidine ($^3$H-TdR) was added to all wells on day 6 and cultures were harvested 18 hours later.

$^3$H-TdR incorporation was assessed using a liquid scintillation counter. Each experiment was conducted in triplicate. $^3$H-TdR incorporation, average cpm for each culture, was determined after subtracting average background cpm. Results are presented in FIG. 7.

FIG. 7 demonstrates that extended life span human dendritic cells, exposed either to IT antigen or PSMA antigen, significantly increased $^3$HTdR incorporation in previously cryopreserved T cell cultures. Thus, it is clear that extended life span DC's are useful to present prostate specific antigen to stimulate autologous T cell proliferation in vitro.

9. EXAMPLE: USE OF A PSMA PEPTIDE TO STIMULATE T CELLS

The ability of a peptide having the amino acid sequence, LLHETDSAV, which corresponds to amino acid residues 4–12 of the PSMA antigen as deduced from cDNA (of the PSMA gene) was assessed in order to determine whether presentation of such antigenic peptide would be useful using the methods of the present invention. The following data show that this antigenic peptide is suitable for use in the methods of the invention.

A peptide having amino acid sequence LLHETDSAV (designated PSMA peptide) was synthesized and purified by Genemed Biotechnologies (San Francisco, Calif.).

One hundred thousand previously frozen T cells (designated "PBMC") obtained from a prostate cancer patient were cultured in the presence or absence of 20 µM PSMA peptide in complete medium containing 10% heat-inactivated human serum and 1 unit/ml IL2. One µCi/well $^3$H-Thymidine was added on day 6 and cultures were harvested 18 hours later. $^3$H-TdR incorporation was counted in a liquid scintillation counter. Each experiment was done in 4 replicates. The average cpm and standard deviation are shown in FIG. 8.

As illustrated in FIG. 8, the antigenic peptide corresponding to amino acid residues 4–12 of PSMA peptide elicited a greatly enhanced T cell proliferation compared to T cells in the absence of this peptide.

The T cells proliferated as a result of the PSMA peptide were expanded in culture for 5 days, in complete medium containing 2 µM PSMA peptide and 1 unit/ml I12 for 5 days prior to harvest. One million cells were incubated for 30 minutes on ice with anti-CD4, anti-CD8 antibodies or medium alone, followed by another 30 minute incubation with fluorescein isothiocyanate labelled-2° antibody. Fluorescence-bound was analyzed in a FACScan (Becton Dickinson, San Jose, Calif.) flow cytometer as described above. The percent CD4+ and CD8+ cells were calculated. Results are illustrated in FIG. 9.

As shown in FIG. 9, the CTL's represented about 41% of the T cells stimulated by the PSMA peptide antigen. Thus, this peptide antigen should be useful to be presented by DC's to T cells to elicit prostate specific responses, both cytolytic (CTL's) and helper (T$_H$ cells against prostate cancer according to the methods of the invention.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for producing a cancer growth inhibiting response, comprising administering, to a prostate cancer patient in need thereof, an effective amount of human dendritic cells, exposed in vitro to a prostate tissue antigen in which the prostate tissue antigen is selected from the group consisting of a lysate of LNCAP cells, a membrane preparation of LNCAP cells, a lysate of prostate tumor cells of the prostate cancer patient, a membrane preparation of prostate tumor cells of the prostate cancer patient, purified prostate specific membrane antigen (PSMA), a peptide having the amino acid sequence LLHETDSAV, a peptide having the amino acid sequence LHBETDSAV, and a peptide having the amino acid sequence LXXXXXXV where X represents any amino acid.

2. The method according to claim 1 in which the prostate tissue antigen is PSMA.

3. The method according to claim 1, in which the human dendritic cells were obtained from skin, spleen, thymus, bone marrow, lymph nodes or peripheral blood of the prostate cancer patient.

4. The method according to claim 1, in which the human dendritic cells were obtained from peripheral blood.

5. The method according to claim 1, in which the dendritic cells were obtained from a healthy individual HLA-matched to the prostate cancer patient.

6. The method according to claim 1, in which the dendritic cells are extended life span dendritic cells.

7. The method according to claim 1, in which the human dendritic cells were cryopreserved and then thawed prior to administration to the prostate cancer patient.

8. The method according to claim 1, in which the prostate cancer patient is suffering from metastatic prostate cancer.

* * * * *